United States Patent
Wang et al.

(10) Patent No.: US 10,537,299 B2
(45) Date of Patent: Jan. 21, 2020

(54) ATTENUATION MAP RECONSTRUCTION FROM TOF PET DATA

(71) Applicant: RENSSELAER POLYTECHNIC INSTITUTE, Troy, NY (US)

(72) Inventors: Ge Wang, Loudonville, NY (US); Qingsong Yang, Troy, NY (US); Wenxiang Cong, Albany, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 219 days.

(21) Appl. No.: 15/579,394

(22) PCT Filed: Jun. 6, 2016

(86) PCT No.: PCT/US2016/036057
§ 371 (c)(1),
(2) Date: Dec. 4, 2017

(87) PCT Pub. No.: WO2016/197127
PCT Pub. Date: Dec. 8, 2016

(65) Prior Publication Data
US 2018/0353147 A1    Dec. 13, 2018

Related U.S. Application Data

(60) Provisional application No. 62/170,893, filed on Jun. 4, 2015.

(51) Int. Cl.
*A61B 6/00*    (2006.01)
*A61B 6/03*    (2006.01)
(Continued)

(52) U.S. Cl.
CPC ............ *A61B 6/5205* (2013.01); *A61B 6/037* (2013.01); *G06T 11/005* (2013.01); *G21H 5/02* (2013.01)

(58) Field of Classification Search
CPC ....... A61B 6/037; A61B 6/481; A61B 6/5205; A61B 6/5258; G06T 11/003; G06T 11/005; G21H 5/02
See application file for complete search history.

(56) References Cited

U.S. PATENT DOCUMENTS 9,600,910 B2 * 3/2017 Wang .................... G01T 1/1647
9,730,657 B2    8/2017 Wang et al.
(Continued)

FOREIGN PATENT DOCUMENTS

WO    2014047446 A1    3/2014
WO    2014074148 A1    5/2014
(Continued)

OTHER PUBLICATIONS

International Search Report/Written Opinion, PCT International Application No. PCT/US2016/036057, PCT/ISA/220, PCT/ISA/210, PCT/ISA/237, dated Sep. 22, 2016.

*Primary Examiner* — Mekonen T Bekele
(74) *Attorney, Agent, or Firm* — Murtha Cullina LLP; Anthony P. Gangemi (57) ABSTRACT

Systems and methods for determining an attenuation sinogram for a time-of-flight (TOF) positron emission tomography (PET) scan using only TOF PET data, and including use of the total amount of tracer provided to the subject of the TOF PET scan, are provided. The total amount of injected tracer can be used to determine the otherwise unknown constant shift present when an attenuation sinogram is estimated using the gradient of the attenuation sinogram. The attenuation sinogram can therefore be accurately and stably determined without any additional knowledge on the attenuation sinogram or map.

20 Claims, 5 Drawing Sheets

(51) Int. Cl.
*G06T 11/00* (2006.01)
*G21H 5/02* (2006.01)

(56) References Cited

U.S. PATENT DOCUMENTS

| | | | |
|---|---|---|---|
| 9,734,600 B2* | 8/2017 | Berker | A61B 6/037 |
| 9,805,481 B2* | 10/2017 | Sperl | G06T 11/005 |
| 9,943,702 B2* | 4/2018 | Kumar | G06F 19/3481 |
| 2011/0015904 A1 | 1/2011 | Fenchel et al. | |
| 2013/0028496 A1* | 1/2013 | Panin | G06T 11/006 382/131 |
| 2013/0109964 A1 | 5/2013 | Kelly | |
| 2015/0036789 A1 | 2/2015 | Panin et al. | |
| 2015/0157286 A1 | 6/2015 | Wang et al. | |
| 2015/0193927 A1* | 7/2015 | Wang | G01T 1/1647 382/131 |
| 2015/0262389 A1* | 9/2015 | Li | G01T 1/1603 382/131 |
| 2016/0113602 A1 | 4/2016 | Wang et al. | |
| 2016/0135769 A1 | 5/2016 | Wang et al. | |
| 2016/0166852 A1 | 6/2016 | Wang et al. | |
| 2017/0043041 A1 | 2/2017 | Wang et al. | |
| 2018/0025512 A1* | 1/2018 | Zhu | G06T 11/008 382/131 |
| 2018/0211419 A1* | 7/2018 | Zhu | A61B 6/037 |
| 2019/0266728 A1* | 8/2019 | Lee | G06T 7/0016 |

FOREIGN PATENT DOCUMENTS

| | | |
|---|---|---|
| WO | WO-2014074148 A1 * | 5/2014 |
| WO | 2015164405 A1 | 10/2015 |
| WO | 2016106348 A1 | 6/2016 |
| WO | 2016118960 A1 | 7/2016 |
| WO | 2016154136 A1 | 9/2016 |
| WO | 2016197127 A1 | 12/2016 |
| WO | 2017015381 A1 | 1/2017 |
| WO | 2017019782 A1 | 2/2017 |
| WO | 2017048856 A1 | 3/2017 |
| WO | 2017083849 A1 | 5/2017 |
| WO | 2017143247 A1 | 8/2017 |
| WO | 2017176976 A1 | 10/2017 |
| WO | 2017205379 A2 | 11/2017 |

* cited by examiner

ATTENUATION MAP RECONSTRUCTION FROM TOF PET DATA

CROSS-REFERENCE TO RELATED APPLICATION

This application is a national stage application of International Patent Application No. PCT/US2016/036057 filed Jun. 6, 2016, which claims the benefit of U.S. Provisional Application Ser. No. 62/170,893, filed Jun. 4, 2015, both of which are incorporated herein by reference in their entireties, including any figures, tables, and drawings.

BACKGROUND OF INVENTION

In quantitative positron emission tomography (PET) imaging, the attenuation background (i.e., map) of the subject (e.g., a human patient or an animal) must be obtained or estimated to accurately reconstruct the radioactive tracer distribution. A PET image reconstructed with an incorrect attenuation map or with no attenuation map would suffer from significant artifacts. Existing methods for estimating the attenuation map of a PET image can be categorized into two general classes: transmission and non-transmission.

Transmission methods are based on transmission data acquired with an external radionuclide source, computed tomography (CT), or magnetic resonance imaging (MRI) scan. In a PET/CT system, attenuation correction is achieved with the CT sub-system. However, there are significant mismatches between a CT image at an average energy of 60-80 kilo-electron-Volts (keV) and a PET attenuation background at 511 keV, and their physical features are quite different, which can cause substantial artifacts. When a correlation map between CT and PET linear attenuation coefficients is established, low dose CT can be used for PET attenuation correction. To compensate for respiratory motion, a long CT acquisition time can be used to obtain an averaged CT attenuation, and a respiratory-gated CT acquisition can help reduce motion artifacts.

Non-transmission methods derive an attenuation map without a separate transmission scan. In the case of brain or abdominal imaging, in which soft tissue is the dominant constituent, a uniform attenuation coefficient is assigned within the tissue contour. In some non-transmission methods, the consistency condition of the Radon transform can be used to estimate regions of fairly uniform attenuation. In some methods, a discrete consistency condition can be utilized for the same purpose. Also, some methods attempt to reconstruct the activity and the attenuation simultaneously based on a statistical model. However, all of these techniques suffer from cross-talk artifacts.

BRIEF SUMMARY

Embodiments of the subject invention provide novel and advantageous systems and methods for determining or estimating an attenuation sinogram and/or attenuation correction map for a time-of-flight (TOF) positron emission tomography (PET) scan using only TOF PET data, and including use of the total amount of tracer provided to the subject of the TOF PET scan. The total amount of provided (e.g., injected) tracer can be used to determine the otherwise unknown constant shift present when an attenuation sinogram is estimated using the gradient (e.g., derivative(s)) of the attenuation sinogram. In this way, the attenuation sinogram, and therefore the attenuation correction map for the TOF PET scan, can be accurately and stably determined or estimated without any additional knowledge on the attenuation sinogram or map.

In one embodiment, a system for performing a TOF PET scan can include: a PET scanner configured to perform TOF PET scanning; at least one processor; and a machine-readable medium, in operable communication with the PET scanner and the at least one processor, having machine-executable instructions stored thereon that, when executed by the at least one processor, perform a method. The method can include: obtaining an initial estimated attenuation singoram of a TOF PET scan, of the PET scanner, that has an unknown constant shift; determining the constant shift of the initial estimated attenuation singoram using the total amount of tracer provided to the subject of the TOF PET scan, wherein determining the constant shift is done without using any further information other than TOF PET scan data; and determining the attenuation sinogram for the TOF PET scan using the determined constant shift and the initial estimated attenuation sinogram.

In another embodiment, a system for determining an attenuation sinogram for TOF PET scan can include: at least one processor; and a machine-readable medium, in operable communication with the at least one processor, having machine-executable instructions stored thereon that, when executed by the at least one processor, perform a method. The method can include: obtaining an initial estimated attenuation singoram of a TOF PET scan that has an unknown constant shift; determining the constant shift of the initial estimated attenuation singoram using the total amount of tracer provided to the subject of the TOF PET scan, wherein determining the constant shift is done without using any further information other than TOF PET scan data; and determining the attenuation sinogram for the TOF PET scan using the determined constant shift and the initial estimated attenuation sinogram.

In another embodiment, a method for performing a TOF PET scan on a subject can include: providing a tracer to the subject to be scanned; scanning the subject in a PET scanner configured to perform TOF PET scanning; and determining an attenuation sinogram for the TOF PET scan. The determining of the attenuation sinogram for the TOF PET scan can include: obtaining an initial estimated attenuation singoram of the TOF PET scan, that has an unknown constant shift; determining the constant shift of the initial estimated attenuation singoram using the total amount of tracer provided to the subject of the TOF PET scan, wherein determining the constant shift is done without using any further information other than TOF PET scan data; and determining the attenuation sinogram for the TOF PET scan using the determined constant shift and the initial estimated attenuation sinogram.

In yet another embodiment, a method of determining an attenuation sinogram for a TOF PET scan can include: obtaining an initial estimated attenuation singoram of the TOF PET scan that has an unknown constant shift; determining the constant shift of the initial estimated attenuation singoram using the total amount of tracer provided to the subject of the TOF PET scan, wherein determining the constant shift is done without using any further information other than TOF PET scan data; and determining the attenuation sinogram for the TOF PET scan using the determined constant shift and the initial estimated attenuation sinogram.

BRIEF DESCRIPTION OF THE DRAWINGS

FIG. 5C shows an image of relative error of the reconstructed attenuation sinogram of FIG. 5B. The scale bar on the right side of FIG. 5C goes from zero (at the bottom) to 18 (the last marked number at the top), and each number marked (in order—2, 4, 6, 8, 10, 12, 14, 16, and 18) is to be multiplied by $10^{-3}$, which is what is indicated just above the scale bar.

DETAILED DESCRIPTION

Embodiments of the subject invention provide novel and advantageous systems and methods for determining or estimating an attenuation sinogram and/or attenuation correction map for a time-of-flight (TOF) positron emission tomography (PET) scan using only TOF PET data, and including use of the total amount of tracer provided to the subject of the TOF PET scan. The total amount of provided (e.g., injected) tracer can be used to determine the otherwise unknown constant shift present when an attenuation sinogram is estimated using the gradient (e.g., derivative(s)) of the attenuation sinogram. In this way, the attenuation sinogram, and therefore the attenuation correction map for the TOF PET scan, can be accurately and stably determined or estimated without any additional knowledge on the attenuation sinogram or map.

In PET, the attenuation correction is important for the reconstruction of a radioactive tracer distribution in a subject (e.g., the body of a human or an animal). Attenuation coefficients can sometimes be computed from a computed tomography (CT) scan in a PET-CT system, but such a CT scan may be inaccurate due to patient motion between the PET and CT scans. Moreover, CT scans can have a negative effect on the patient's health due to ionizing radiation from the high radiation dose of the CT device. A PET image reconstructed with an incorrect attenuation map or without this information would suffer from significant attenuation artifacts. TOF-PET has been around for many years but only recently has been used in practice, due to ultrafast electronics and improved scintillation materials. In TOF PET, a pair of photons from an annihilation location is measured in a time-resolving fashion. TOF-PET data contain important information on attenuation coefficients, but no existing method can estimate the absolute attenuation sinogram from TOF PET data.

Embodiments of the subject invention can directly estimate the attenuation sinogram of a TOF PET scan using only TOF PET data (i.e., no external data other than the TOF PET data). In conventional algorithms, the gradient of the attenuation sinogram can be estimated using the current algorithm, and the attenuation sinogram computed from derivatives of the attenuation sinogram has an unknown constant shift. In many embodiments of the subject invention, a compensatory method using the total amount of injected tracer can be used to determine the constant shift. An attenuation sinogram and the attenuation correction map can be accurately and stably determined or estimated without any additional knowledge on the attenuation sinogram or map.

During a PET scan, a tracer (e.g., a radioactive tracer isotope) can be provided to (e.g., injected into) the subject to be scanned (e.g., injected blood circulation). Each tracer atom can be chemically incorporated into one or more biologically active molecule. After the active molecule(s) become(s) concentrated in tissues of interest within the subject, the subject is then scanned using the PET imaging scanner. During the scan, a record of tissue concentration can be made as the tracer decays. As the tracer undergoes positron emission decay, it emits a positron, which is an antiparticle of an electron and has opposite charge. The emitted positron travels in tissue for a short distance, loses its kinetic energy, and decelerates until it interacts with an electron. The interaction annihilates both the electron and the positron, producing a pair of annihilation photons moving in approximately opposite directions. These are detected when they reach a scintillator in the scanning device, creating a burst of light that is detected by the device. The technique depends on simultaneous or coincident detection of the pair of photons moving in approximately opposite directions. The scanner can have a built-in direction-error tolerance because the directions of the photons, while they can be exactly opposite in their center of mass frame, the scanner has no way to determine this. Photons that do not arrive in temporal "pairs" (i.e., within a timing-window of, for example, a few nanoseconds) are ignored.

The raw data collected by a PET scanner are a list of "coincidence events" of near-simultaneous detection of annihilation photon pairs. Each coincidence event represents a line in space connecting the two detection points of the scanner along which the positron emission occurred, known as the line of response (LOR). TOF can be used to more precisely determine the difference in time between the detection of the two photons and can thus localize the point of origin of the annihilation event between the two detection points of the scanner to within a very small area. Coincidence events can be grouped into projection images, called sonograms, and the sinograms can be sorted by the angle of each view and tilt (for 3D images). The sinogram images are similar to the projections captured by CT scanners, but they can have more noise due to a lower number of acquired data points. Two major sources of noise in PET are scatter (a detected pair of photons, at least one of which was deflected from its original path by interaction with matter in the field of view, leading to the pair being assigned to an incorrect LOR) and random events (e.g., photons originating from two different annihilation events but incorrectly recorded as a coincidence pair because their arrival at their respective detectors occurred within a coincidence timing window). Pre-processing of the data can be performed to correct for random coincidences, estimate and subtract scattered photons, correct for detector dead-time (the time immediately after detection of a photon), and/or correct for detector sensitivity (both inherent and due to angle of incidence).

During PET, attenuation occurs, for example, when photons emitted by the tracer inside the subject are absorbed by intervening tissue (or other mass) between the detector and the emission point. As different LORs travel different thicknesses of tissue, the photons are attenuated differently, which can lead to structures deep in the body being reconstructed as having falsely low tracer uptake, if the attenuation is not accounted for (e.g., by reconstructing an attenuation map).

PET scanners typically include multiple detector rings, forming a cylindrical or cylinder-like shape around a subject to be scanned. In two-dimensional (2D) reconstruction, each ring is treated as a separate entity, so that only coincidences within a ring are detected, and the image from each ring can be reconstructed individually. In three-dimensional (3D) reconstruction, coincidences can be detected between rings and within rings, and the entire volume can be reconstructed together. 3D reconstruction can have better sensitivity and potentially less noise, but typically require greater computing resources.

For a positron emission event, the total tracer injection can be represented by $N_0$, and the total tracer at time T can be determined by Equation (1).

$$N(T) = N_0 e^{-\lambda T} \quad (1)$$

The total event rate at time T can be calculated from $$-\frac{dN(T)}{dT} = \lambda N_0 e^{-\lambda T}, \quad (2)$$

and the total event at time T can be calculated from $$E(T) = -\frac{dN(T)}{dT} \cdot \Delta T = \lambda N_0 \Delta T e^{-\lambda T}. \quad (3)$$

Time-of-flight (TOF) PET measures a pair of photons from an annihilation location in a time-resolving fashion, thereby providing a better localization of coincidence events along the line-of-response (LOR) than with conventional PET. TOF-PET data contain important information on attenuation coefficients, and reconstruction algorithms (e.g., maximum-a-posterior reconstruction algorithms) can be used to attempt to simultaneously reconstruct both tracer concentrations and attenuation coefficients from a TOF-PET scan. The gradient of an attenuation sinogram can be uniquely computable only from TOF PET data, but a constant offset appears in the process of integrating the gradient of the original sinogram. No existing method is capable of estimating the absolute attenuation background (attenuation map) from only from the gradient of the attenuation sinogram. In embodiments of the subject invention, prior knowledge of the attenuation background can be used to find this constant offset term that appears when integrating the gradient of the original sinogram of a TOF PET scan. In particular, the constant uncertainty for self-sufficient TOF PET imaging can be eliminated by using the total amount of injected tracer as prior information (i.e., prior knowledge of the attenuation background). TOF-PET data can accurately determine an attenuation sinogram for PET attenuation correction with or without any additional knowledge beyond this prior knowledge of the attenuation background.

A radioactive tracer distribution can be denoted as f(x, y). In 2D TOF-PET, the measurement data along a line of response (LOR) can be expressed as $$m(\theta, s, t) = p(\theta, s, t) \exp(-g(\theta, s)), \quad (4)$$

where p (θ, s, t) is the 2D TOF data of a tracer distribution f(x, y) that can be formulated as, $$p(\theta, s, t) = \int_{-\infty}^{\infty} f(s \cdot \cos\theta - l \cdot \sin\theta, s \cdot \sin\theta + l \cdot \cos\theta) w(t-l) dl, \quad (5)$$

where w(t) is a TOF time profile, which is, for example, assumed as a Gaussian function with a standard deviation σ<∞, $$w(t) = \frac{1}{\sqrt{2\pi}\,\sigma} e^{-t^2/2\sigma^2}. \quad (6)$$

and g(θ, t) is the Radon transform of the attenuation coefficients μ(x, y), $$g(\theta, s) = \int_{-\infty}^{\infty} \mu(s \cdot \cos\theta - l \cdot \sin\theta, s \cdot \sin\theta + l \cdot \cos\theta) dl. \quad (7)$$

The differential attenuation sonogram can be determined from TOF PET data alone, and Theorem 1 summarizes this (see also Defrise et al., *Physics in Medicine and Biology*, 57(4), 885-899, 2012, which is hereby incorporated by reference in its entirety).

Theorem 1: The emission data m(θ, s, t) determine derivatives of the Radon transform g(θ, s) over θ and s if: (1) the TOF time profile is a Gaussian function; (2) for each measured line of response (LOR), the TOF data are measured for all $t \in \mathbb{R}$; (3) f(x, y) and μ(x, y) are non-negative functions with continuous first derivatives and bounded supports; and (4) no LOR is totally attenuated so that $e^{g(\theta,s)} > 0$ for all θ and s.

Based on the proof of the theorem, an analytical scheme for estimation of the gradient of the attenuation sinogram is given as follows:

$$\frac{\partial g}{\partial s} = -\frac{J_s H_{\theta\theta} - J_\theta H_{s\theta}}{H_{ss} H_{\theta\theta} - H_{s\theta}^2} \quad (8)$$

$$\frac{\partial g}{\partial \theta} = -\frac{J_\theta H_{ss} - J_s H_{s\theta}}{H_{ss} H_{\theta\theta} - H_{s\theta}^2}$$

where $$H_{ss} = \int_\tau (mt + \sigma^2 \partial_t m)^2 dt, \quad H_{s\theta} = \int_\tau m(mt + \sigma^2 \partial_t m) dt, \quad (9)$$

$$H_{\theta\theta} = \int_\tau m^2 dt, \quad J_s = \int_\tau (D[m])(mt + \sigma^2 \partial_t m) dt, \quad J_\theta = \int_\tau (D[m]) m \, dt,$$

and the operator D[•] is defined as $$D[m(\theta, s, t)] = t \frac{\partial m}{\partial s} + \frac{\partial m}{\partial \theta} - s \frac{\partial m}{\partial t} + \sigma^2 \frac{\partial^2 m}{\partial s \partial t}. \quad (10)$$

Theorem 2: From derivatives of the Radon transform, the emission data determine the Radon transform Rμ of the attenuation image up to an additive constant within the sinogram region d defined as the set of LORs that contain activity: $\Omega = \{(\theta, s) \in [0, \pi) \times R | m(\theta, s, t) > 0\}$.

In many embodiments of the subject invention, the following Theorem 3 can be used to determine the attenuation map of a TOF-PET scan. Theorem 3 can be used, for example, in conjunction with Theorem 1 and Theorem 2.

Theorem 3: The additive constant of Theorem 2 can be estimated using the total amount of injected tracer as prior information based on derivative data of the Radon transform, and the Radon transform of the attenuation image can be determined from the emission data.

From Equation (8), the derivative of attenuation sinogram $$\frac{\partial g}{\partial s}$$

can be calculated, and the attenuation sinogram can be recovered up to a constant based on Theorem 2, $$g(s,\theta)=g'(s,\theta)+C(\theta) \quad (11)$$

In this context, methods of many embodiments of the subject invention determine the constant C using the total amount of injected tracer as prior information. From Equations (4)-(7), the tracer emission is proportional to the tracer density. The PET measurement along (s, θ) line path is $$m(\theta,s)=\int_{-\infty}^{\infty}(s\cdot\cos\theta-l\cdot\sin\theta,s\sin\theta+l\cdot\cos\theta)dl\times\exp(-(s,\theta)) \quad (12)$$

Substituting Equation (11) into Equation (12) gives $$m(\theta,s)\exp(g'(s,\theta)+C(\theta))=\int_{-\infty}^{\infty}f(s\cdot\cos\theta-l\cdot\sin\theta,s\cdot\sin\theta+l\cdot\cos\theta)dl. \quad (13)$$

Integrating along s on both sides of Equation (13), $$e^{C(\theta)}\int_s m(\theta,s)\exp(g'(s,\theta))ds=\int\int_{-\infty}^{\infty}f(s\cdot\cos\theta-l\cdot\sin\theta,s\cdot\sin\theta+l\cdot\cos\theta)dlds=P \quad (14)$$

where P is the total amount of the injected tracer. From Equation (14), the constant offset $C(\theta)$ can be estimated from the measurement of emission events for each projection view.

Figure 1:
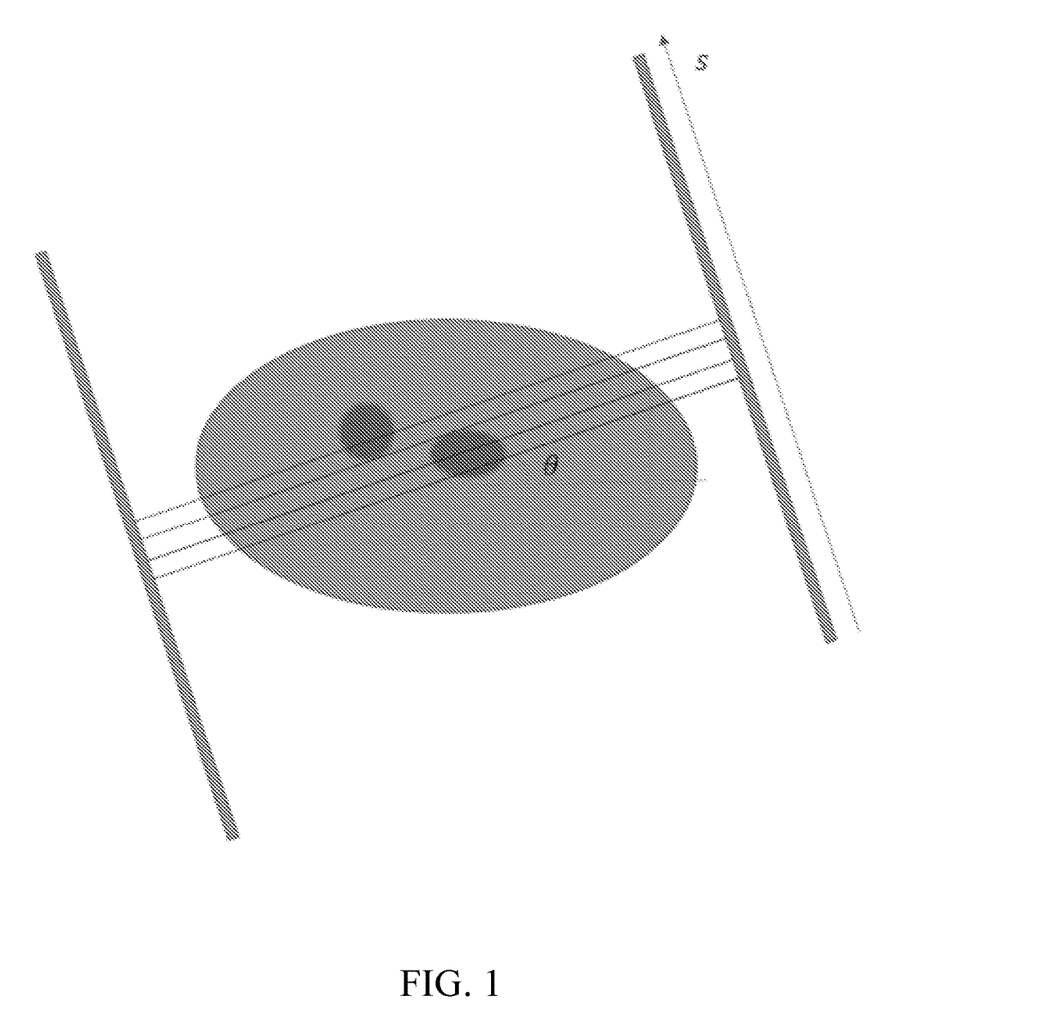
FIG. 1 shows a visual representation of two hotspots in a two-dimensional (2D) PET scan.

In certain embodiments, the total-tracer-amount-based estimation of a PET attenuation map assumes that a whole body (e.g., entire subject) PET scan is continuously performed so that the total amount of the trace is under global monitoring. Initially, there may be only one hot spot, which can guide the attenuation map estimation as described herein. Once the hot spot is divided into two immediately adjacent (or approximately adjacent) smaller hot spots, the contact point can be identified in an appropriate projection view, as shown in FIG. 1 and discussed in Examples 1 and 2, and this may give little or no emission data. Then, the total amounts of the two smaller hot spots can be estimated from this projection and used for attenuation estimation along any lines through these two smaller hot spots. This process can be repeated to handle isolated hot spots in the subject (e.g., human or animal body).

In some embodiments, data preprocessing steps can be performed, such as for scattering correction, to provide even better results. Also, other relevant techniques can be combined with the approach discussed herein to further improve accuracy and reliability; for example, use of more consistence based derivatives and/or estimation of electron density from scatter events can be performed.

Systems and methods of embodiments of the subject invention use the total amount of provided (e.g., injected) tracer to determine the constant shift of an attenuation sinogram computed from derivatives (the gradient) of the attenuation sinogram. An attenuation sinogram and the attenuation correction map can be accurately and stably determined or estimated without any specific knowledge on it.

To reconstruct a radioactive tracer distribution from a PET scan, the background attenuation correction is needed to eliminate image artifacts. TOF PET data can determine the attenuation sinogram up to a constant, and embodiments of the subject invention can determine or eliminate this constant, thereby directly estimating or determining the attenuation sinogram (and attenuation map) only from TOF PET data using the total amount of provided (e.g., injected) tracer.

PET is a noninvasive medical imaging technology used for a variety of clinical applications in, for example, oncology, neurology, and cardiology. In PET imaging, coincident gamma rays (annihilation rays) are emitted from the annihilation of a positron from a tracer provided to (e.g., injected into) the subject (e.g., a human or animal patient). The gamma rays are detected by the PET scanner, and tomographic images are created through, for example, filtered back projection, or an iterative series of back and forward projection steps. In a TOF PET scanner, the arrival times of each coincident pair of photons are more precisely known, and the difference between them is used to localize the annihilation event along the line between the two detected photons. PET can be used to localize malignant tumors, and generate high-resolution images of human and animal physiological functions. TOF PET is an improvement over traditional PET that uses the time difference in detection of the two photon events. TOF information provides better localization of the annihilation event along the line formed by each detector pair, resulting in an overall improvement in signal to noise ratio (SNR) of the reconstructed image. Embodiments of the subject invention provide a direct estimation of the attenuation sinogram only from TOF PET data. In some algorithms, the gradient of the attenuation sinogram can be estimated using the current algorithm, and the attenuation sinogram computed from derivatives of the attenuation sinogram has an unknown constant shift. In embodiments of the subject invention, The total amount of injected tracer can be used to determine the constant shift, thereby providing accurate and stable determination or estimation of an attenuation sinogram and the attenuation correction map without any specific knowledge on it.

The methods and processes described herein can be embodied as code and/or data. The software code and data described herein can be stored on one or more computer-readable media or machine-readable media, which may include any device or medium that can store code and/or data for use by a computer system. When a computer system reads and executes the code and/or data stored on a computer-readable medium, the computer system performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The subject invention includes, but is not limited to, the following exemplified embodiments.

Embodiment 1

A system for performing a time-of-flight (TOF) positron emission tomography (PET) scan, the system comprising:

a PET scanner configured to perform TOF PET scanning;
at least one processor; and
a machine-readable medium, in operable communication with the PET scanner and the at least one processor, having machine-executable instructions stored thereon that, when executed by the at least one processor, perform a method, the method comprising:
obtaining an initial estimated attenuation singoram of a TOF PET scan, of the PET scanner, that has an unknown constant shift;
determining the constant shift of the initial estimated attenuation singoram using the total amount of tracer provided (e.g., injected) to the subject (e.g., a human or animal patient) of the TOF PET scan, wherein determining the constant shift is done without using any further information other than TOF PET scan data; and
determining (or estimating) the attenuation sinogram for the TOF PET scan using the determined constant shift and the initial estimated attenuation sinogram.

Embodiment 2

The system according to embodiment 1, wherein the method executed by the at least one processor further comprises:
reconstructing the TOF PET image using the attenuation sinogram and TOF PET data from the TOF PET scan.

Embodiment 3

The system according to embodiment 2, wherein the method executed by the at least one processor further comprises:
performing pre-processing of the TOF PET data, before reconstructing the TOF PET image, to correct for random coincidences, estimate and subtract scattered photons, correct for detector dead-time, and/or correct for detector sensitivity.

Embodiment 4

The system according to any of embodiments 1-3, wherein determining the constant shift of the initial estimated attenuation singoram using the total amount of tracer provided to the subject comprises using the following equation:

$$e^{C(\theta)} \int_s m(\theta,s) \exp(g'(s,\theta)) ds = \int \int_{-\infty}^{\infty} f(s \cdot \cos\theta - l \cdot \sin\theta, s \cdot \sin\theta + l \cdot \cos\theta) dl ds = P,$$

where $m(\theta, s)$ is emission data along a path $(\theta, s)$, where $\theta$ is an angle of the path and s is a distance along the path, where $g'(s, \theta)$ is the derivative of the Radon transform, where $f(x,y)$ is a distribution of the tracer, where $C(\theta)$ is the constant shift of the initial estimated attenuation singoram, and where P is the total amount of tracer provided to the subject.

Embodiment 5

The system according to any of embodiments 1-4, wherein the system is configured for two-dimensional (2D) image reconstruction.

Embodiment 6

The system according to any of embodiments 1-4, wherein the system is configured for three-dimensional (3D) image reconstruction.

Embodiment 7

The system according to any of embodiments 1-6, wherein the system is configured to perform a scan on a human patient.

Embodiment 8

The system according to any of embodiments 1-6, wherein the system is configured to perform a scan on a non-human animal patient.

Embodiment 9

The system according to any of embodiments 1-6, wherein the system is configured to perform a scan on a human patient or a non-human animal patient.

Embodiment 10

The system according to any of embodiments 1-9, further comprising a memory in operable communication with the processor and the machine-readable medium.

Embodiment 11

The system according to embodiment 10, wherein the memory stores the TOF PET scan data.

Embodiment 12

The system according to any of embodiments 10-11, wherein the memory stores data of the total amount of tracer provided to the subject of the TOF PET scan.

Embodiment 13

The system according to any of embodiments 1-12, further comprising a display in operable communication with the processor and the machine-readable medium.

Embodiment 14

The system according to embodiment 13, wherein the display displays to a user of the system the determined (or estimated) attenuation sinogram for the TOF PET scan.

Embodiment 15

The system according to any of embodiments 13-14, wherein the display displays to a user of the system the reconstructed TOF PET image.

Embodiment 16

The system according to any of embodiments 1-15, wherein the PET scanner comprises a plurality of scanning rings, forming a generally cylindrical shape of scanning rings, wherein each scanning ring comprises a scintillating material on an inner surface thereof.

Embodiment 17

A system for determining (or estimating) an attenuation sinogram for a time-of-flight (TOF) positron emission tomography (PET) scan, the system comprising:
at least one processor; and a machine-readable medium, in operable communication with the at least one processor, having machine-executable instructions stored thereon that, when executed by the at least one processor, perform a method, the method comprising:
  obtaining an initial estimated attenuation singoram of a TOF PET scan that has an unknown constant shift;
  determining the constant shift of the initial estimated attenuation singoram using the total amount of tracer provided (e.g., injected) to the subject (e.g., a human or animal patient) of the TOF PET scan, wherein determining the constant shift is done without using any further information other than TOF PET scan data; and
  determining (or estimating) the attenuation sinogram for the TOF PET scan using the determined constant shift and the initial estimated attenuation sinogram.

Embodiment 18

The system according to embodiment 17, wherein determining the constant shift of the initial estimated attenuation singoram using the total amount of tracer provided to the subject comprises using the following equation:

$$e^{C(\theta)}\int_s m(\theta,s)\exp(g'(s,\theta))ds = \int\int_{-\infty}^{\infty} f(s\cdot\cos\theta - l\cdot\sin\theta, s\cdot\sin\theta + l\cdot\cos\theta)dlds = P,$$

where $m(\theta, s)$ is emission data along a path $(\theta, s)$, where $\theta$ is an angle of the path and $s$ is a distance along the path, where $g'(s, \theta)$ is the derivative of the Radon transform, where $f(x,y)$ is a distribution of the tracer, where $C(\theta)$ is the constant shift of the initial estimated attenuation singoram, and where $P$ is the total amount of tracer provided to the subject.

Embodiment 19

The system according to any of embodiments 17-18, wherein the system is configured to determine (or estimate) the attenuation sinogram for the TOF PET scan based on a 2D image reconstruction mode.

Embodiment 20

The system according to any of embodiments 17-18, wherein the system is configured to determine (or estimate) the attenuation sinogram for the TOF PET scan based on a 3D image reconstruction mode.

Embodiment 21

The system according to any of embodiments 17-20, further comprising a memory in operable communication with the processor and the machine-readable medium.

Embodiment 22

The system according to embodiment 21, wherein the memory stores the TOF PET scan data.

Embodiment 23

The system according to any of embodiments 21-22, wherein the memory stores data of the total amount of tracer provided to the subject of the TOF PET scan.

Embodiment 24

The system according to any of embodiments 17-23, further comprising a display in operable communication with the processor and the machine-readable medium.

Embodiment 25

The system according to embodiment 24, wherein the display displays to a user of the system the determined (or estimated) attenuation sinogram for the TOF PET scan.

Embodiment 26

The system according to any of embodiments 24-25, wherein the display displays to a user of the system the reconstructed TOF PET image.

Embodiment 27

A method for performing a time-of-flight (TOF) positron emission tomography (PET) scan on a subject, the method comprising:
  providing a tracer to the subject to be scanned;
  scanning the subject in a PET scanner configured to perform TOF PET scanning; and
  determining (or estimating) an attenuation sinogram for the TOF PET scan,
  wherein determining (or estimating) the attenuation sinogram for the TOF PET scan comprises:
    obtaining an initial estimated attenuation singoram of the TOF PET scan, that has an unknown constant shift;
    determining the constant shift of the initial estimated attenuation singoram using the total amount of tracer provided to the subject of the TOF PET scan, wherein determining the constant shift is done without using any further information other than TOF PET scan data; and
    determining (or estimating) the attenuation sinogram for the TOF PET scan using the determined constant shift and the initial estimated attenuation sinogram.

Embodiment 28

The method according to embodiment 27, further comprising:
  reconstructing the TOF PET image using the attenuation sinogram and TOF PET data from the TOF PET scan.

Embodiment 29

The method according to embodiment 28, further comprising:
  performing pre-processing of the TOF PET data, before reconstructing the TOF PET image, to correct for random coincidences, estimate and subtract scattered photons, correct for detector dead-time, and/or correct for detector sensitivity.

Embodiment 30

The method according to any of embodiments 27-29, wherein determining the constant shift of the initial estimated attenuation singoram using the total amount of tracer provided to the subject comprises using the following equation:

$e^{C(\theta)} \int_s m(\theta,s)\exp(g'(s,\theta))ds = \int\int_{-\infty}^{\infty} f(s\cdot\cos\theta - l\cdot\sin\theta, s\cdot\sin\theta + l\cdot\cos\theta)dlds = P,$ where m(θ, s) is emission data along a path (θ, s), where θ is an angle of the path and s is a distance along the path, where g'(s, θ) is the derivative of the Radon transform, where f(x,y) is a distribution of the tracer, where C(θ) is the constant shift of the initial estimated attenuation singoram, and where P is the total amount of tracer provided to the subject.

Embodiment 31

The method according to any of embodiments 28-30, wherein the image is reconstructed using 2D image reconstruction.

Embodiment 32

The method according to any of embodiments 28-30, wherein the image is reconstructed using 3D image reconstruction.

Embodiment 33

The method according to any of embodiments 27-32, wherein the subject is a human patient.

Embodiment 34

The method according to any of embodiments 27-32, wherein the subject is a non-human animal patient.

Embodiment 35

The method according to any of embodiments 27-32, wherein the subject is a human patient or a non-human animal patient.

Embodiment 36

The method according to any of embodiments 27-35, further comprising storing the TOF PET scan data on a memory.

Embodiment 37

The method according to any of embodiments 27-36, further comprising storing data of the total amount of tracer provided to the subject of the TOF PET scan on a memory (which may be the same or different memory from that recited in embodiment 36).

Embodiment 38

The method according to any of embodiments 27-37, further comprising displaying the determined (or estimated) attenuation sinogram for the TOF PET scan.

Embodiment 39

The method according to any of embodiments 28-38, further comprising displaying the reconstructed TOF PET image.

Embodiment 40

The method according to any of embodiments 27-39, wherein the PET scanner comprises a plurality of scanning rings, forming a generally cylindrical shape of scanning rings, wherein each scanning ring comprises a scintillating material on an inner surface thereof.

Embodiment 41

The method according to any of embodiments 27-40, wherein providing the tracer to the subject comprises injecting the subject with the tracer.

Embodiment 42

The method according to any of embodiments 27-41, wherein the tracer is a radioactive tracer.

Embodiment 43

A method of determining (or estimating) an attenuation sinogram for a time-of-flight (TOF) positron emission tomography (PET) scan, the method comprising:
obtaining an initial estimated attenuation singoram of the TOF PET scan that has an unknown constant shift;
determining the constant shift of the initial estimated attenuation singoram using the total amount of tracer provided (e.g., injected) to the subject (e.g., a human or animal patient) of the TOF PET scan, wherein determining the constant shift is done without using any further information other than TOF PET scan data; and
determining (or estimating) the attenuation sinogram for the TOF PET scan using the determined constant shift and the initial estimated attenuation sinogram.

Embodiment 44

The method according to embodiment 43, wherein determining the constant shift of the initial estimated attenuation singoram using the total amount of tracer provided to the subject comprises using the following equation:

$e^{C(\theta)} \int_s m(\theta,s)\exp(g'(s,\theta))ds = \int\int_{-\infty}^{\infty} f(s\cdot\cos\theta - l\cdot\sin\theta, s\cdot\sin\theta + l\cdot\cos\theta)dlds = P,$ where m(θ, s) is emission data along a path (θ, s), where θ is an angle of the path and s is a distance along the path, where g'(s, θ) is the derivative of the Radon transform, where f(x,y) is a distribution of the tracer, where C(θ) is the constant shift of the initial estimated attenuation singoram, and where P is the total amount of tracer provided to the subject.

Embodiment 45

A method of reconstructing a TOF PET image of a TOF PET scan, the method comprising:
determining (or estimating) the attenuation sinogram of the TOF PET image using the method according to any of embodiments 43-44; and
reconstructing the TOF PET image using the attenuation sinogram and TOF PET data from the TOF PET scan.

Embodiment 46

The method according to embodiment 45, further comprising performing pre-processing of the TOF PET data, before reconstructing the TOF PET image, to correct for random coincidences, estimate and subtract scattered photons, correct for detector dead-time, and/or correct for detector sensitivity.

Embodiment 47

The method according to any of embodiments 45-46, wherein the image is reconstructed using 2D image reconstruction.

Embodiment 48

The method according to any of embodiments 45-46, wherein the image is reconstructed using 3D image reconstruction.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Example 1

Figure 2:
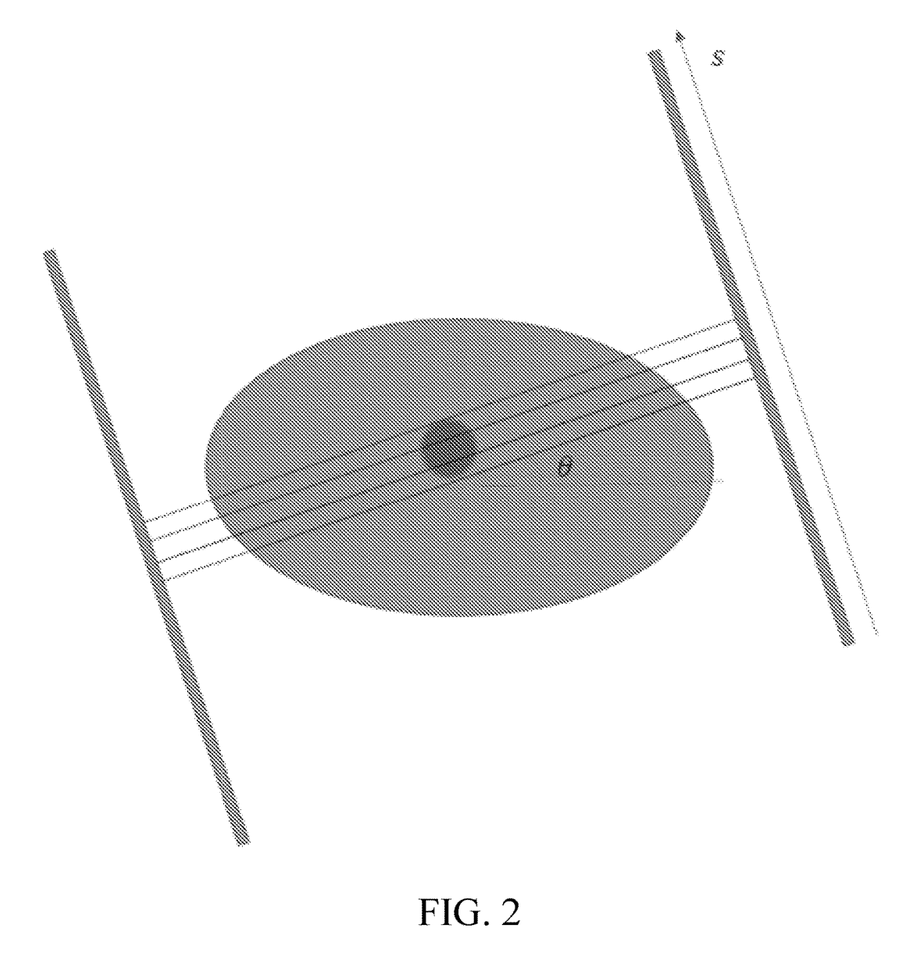
FIG. 2 shows a visual representation of one hotspot in a 2D PET scan.

A two-dimensional (2D) scan reconstruction with one hotspot was considered. FIG. 2 shows a visual representation of one hotspot in a 2D PET scan. The measurement can be represented by $$m(s,\theta,t)=\{E(s,\theta,t)\times\omega(t)\}\exp(-a(s,\theta)) \quad (15)$$

where $\omega(t)$ is the TOF profile and can be modeled as a Gaussian function, and $E(s, \theta, t)$ represents the emission event counts that happen at position $(s, \theta, t)$ and travel along direction $(s, \theta)$.

To estimate the derivative of $a(s, \theta)$, the Equation (16) can be used:

$$H_{ss}=\int_t d(mt+\sigma^2 m_j)^2, H_{s\phi}=\int_t dtm(mt+\sigma^2 m_t), H_{\phi\phi}=\int_t dtm^2,$$

$$J_s=\int_t dt(\mathcal{D}m)(mt+\sigma^2 m_j), J_\phi=\int_t dt(\mathcal{D}m)m. \quad (16)$$

Then, the unweighted least-squares estimates of the derivatives are as follows.

$$\frac{\partial(\mathcal{R}\mu)(\phi,s)}{\partial s}=-\frac{J_s H_{\phi\phi}-J_\phi H_{s\phi}}{H_{ss}H_{\phi\phi}-H_{s\phi}^2}, \quad \frac{\partial(\mathcal{R}\mu)(\phi,s)}{\partial \phi}=-\frac{J_\phi H_{ss}-J_s H_{s\phi}}{H_{ss}H_{\phi\phi}-H_{s\phi}^2}. \quad (17)$$

$$\mathcal{D}p = t\frac{\partial p}{\partial s}+\frac{\partial p}{\partial \phi}-s\frac{\partial p}{\partial t}+\sigma^2\frac{\partial^2 p}{\partial s\partial t}=0. \quad (18)$$

The derivative of the attenuation can be estimated from TOF data:

$$m(s,\theta,t)=[E(s,\theta,t)\otimes\omega(t)]\exp(-a'(s,\theta)+C(\theta)) \quad (19)$$

Considering non-TOF data, $$m(s,\theta)=E(s,\theta)\exp(-a'(s,\theta)+C(\theta)) \quad (20)$$

$$\int_s m(s,\theta)\exp(a'(s,\theta))=\exp(C(\theta))\int_s E(s,\theta) \quad (21)$$

If $\int_s E(s,\theta)$ is known, the constant $C(\theta)$ can be determined.

Example 2

A 2D scan reconstruction with two hotspots was considered. FIG. 1 shows a visual representation of two hotspots in a 2D PET scan. A critical angle where the two hotspots are just separated can be determined, and the constant can be estimated at this angle. The concentration of the two hotspots can be estimated separately, and the constant can then be estimated at other angles. If more hotspots are present, it may be the case that the constant cannot be directly calculated. The diffusion function of tracer in the subject can be used.

Example 3

Figure 3:
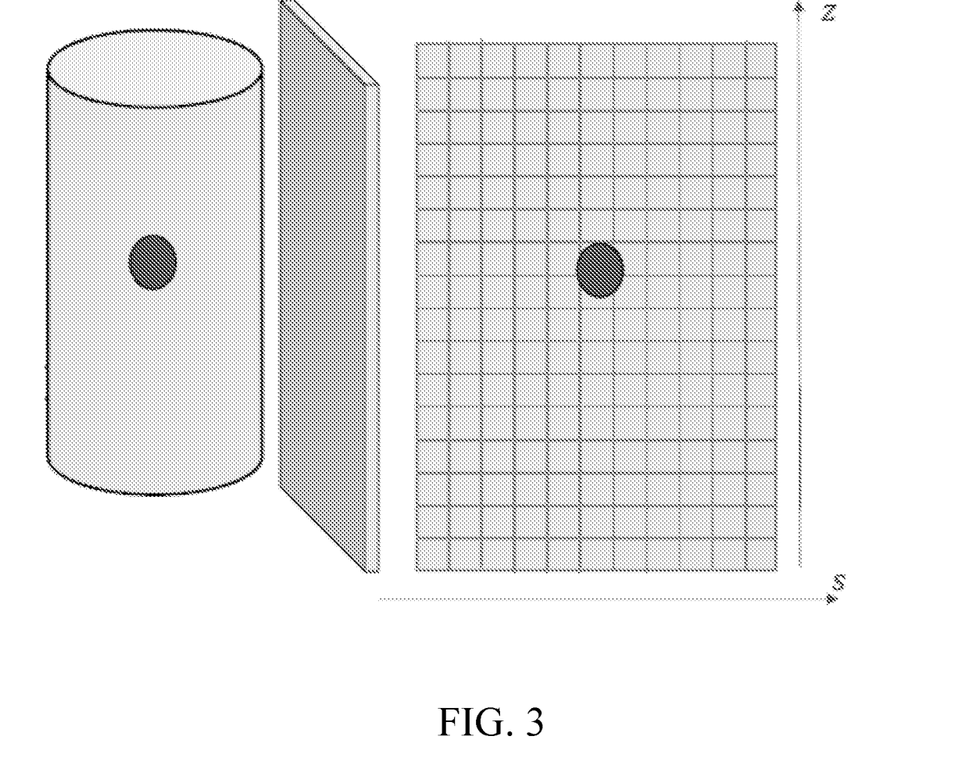
FIG. 3 shows a visual representation of a three-dimensional (3D) PET scan.

A three-dimensional (3D) scan reconstruction with was considered. FIG. 3 shows a visual representation of a 3D PET scan. Screen projection was considered. The directive along s and z can be estimated.

$$m(s,z,\theta,t)=\{E(s,z,\theta,t)\times\omega(t)\}\exp(-a'(s,z,\theta)+C(\theta)) \quad (22)$$

Considering non-TOF data, $$\int_s m(s,z,\theta)\exp(a'(s,z,\theta))=\exp(C(\theta))E(s,z,\theta))\int_s E(s,z,\theta) \quad (23)$$

If $\int_s E(s,z,\theta)$ is known, the constant $C(\theta)$ can be eliminated.

Example 4

Figure 4:
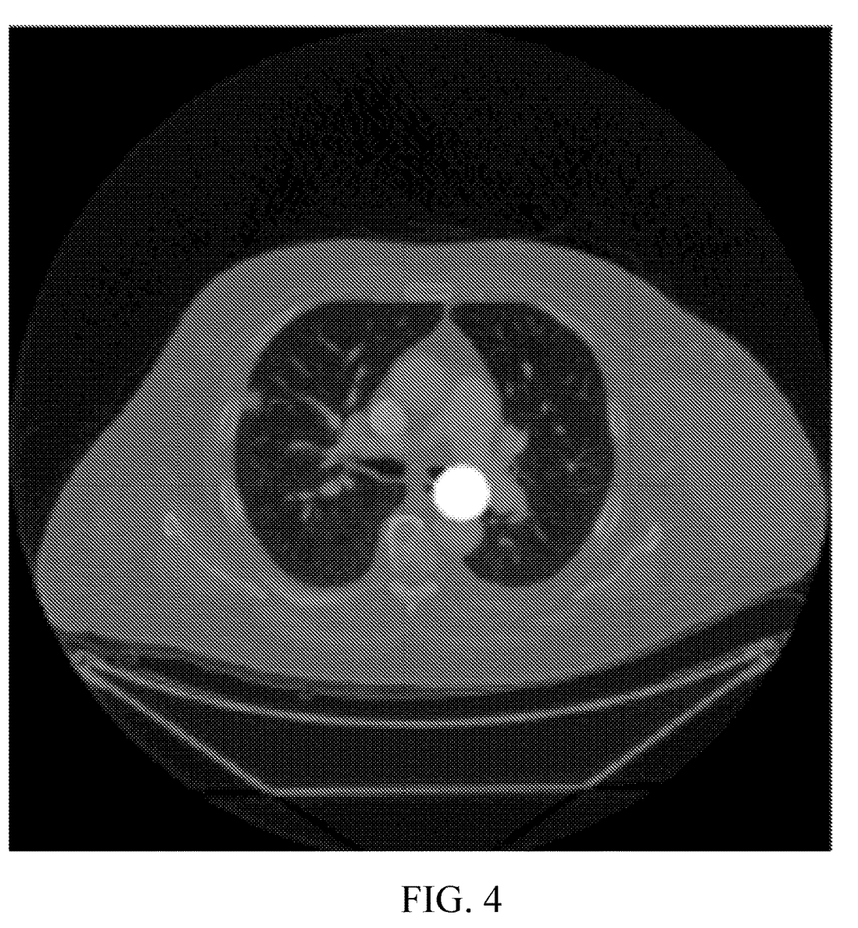
FIG. 4 shows an image of a phantom of a tracer distribution and an attenuation background.
Figure 5A:
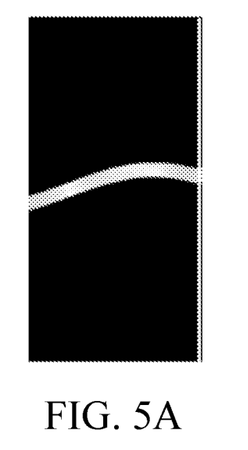
FIG. 5A shows an image of a true attenuation sinogram.
Figure 5B:
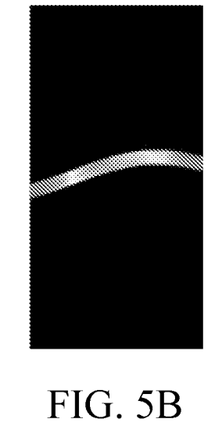
FIG. 5B shows an image of a reconstructed attenuation sinogram.
Figure 5C:
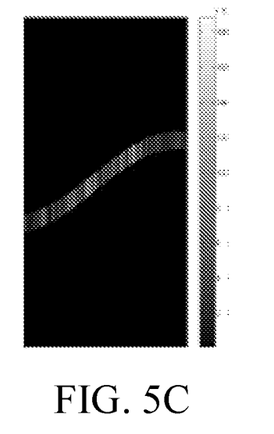

To verify the attenuation estimation based on Equation (14), a 2D TOF PET study was numerically performed. A human chest numerical phantom was used for the simulation, as shown in FIG. 4. The field of view (FOV) was set to 40 cm in diameter and was sampled into an image of 512×512 pixels with a pixel size of 0.05 cm. TOF-PET data were synthesized by convolving the image with the Gaussian profile of a standard deviation of $$\sigma_t = \frac{FWHM}{2\sqrt{2\ln 2}}, \quad (24)$$

where FWHM is the full-width at half-maximum of the Gaussian profile corresponding to a timing resolution of about 500 picoseconds (ps) FWHM. A number of detectors of 1024 was assumed, along with 360 view angles over a 180 angular range and 128 time bins covering the FOV. The derivatives of the attenuation sinogram along the s direction were estimated using Equation (9). While there is an offset of the attenuation map from the estimated differential attenuation sinogram for each projection view, using the total amount of the injected tracer as prior information, the attenuation map was accurately reconstructed based on Equation (14), giving a maximum relative error of 2%. FIG. 5A shows an image of the true attenuation sinogram, and FIG. 5B shows an image of the reconstructed attenuation sinogram using the method described herein (based on Equation (14)). FIG. 5C shows an image of relative error of the reconstructed attenuation sinogram of FIG. 5B compared to the true sinogram of FIG. 5A. The scale bar on the right side of FIG. 5C goes from zero (at the bottom) to 18 (the last marked number at the top), and each number marked (in order—2, 4, 6, 8, 10, 12, 14, 16, and 18) is to be multiplied by $10^{-3}$, which is what is indicated just above the scale bar.

Referring to FIGS. 5A, 5B, and 5C, the reconstructed attenuation sinogram agrees very closely with the true attenuation sinogram, with minimal error and noise.

Figure 6A:
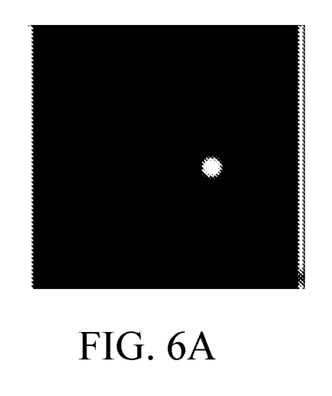
FIG. 6A shows an image of a true tracer distribution.

Based on the reconstructed attenuation map, the distribution of tracer in the phantom was reconstructed. FIG. 6A shows an image of the true tracer distribution, and FIG. 6B shows an image of the reconstructed tracer distribution.

Figure 6B:
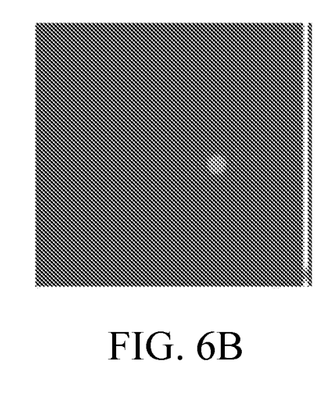
FIG. 6B shows an image of a reconstructed tracer distribution.

Referring to FIGS. 6A and 6B, the reconstructed tracer distribution agrees closely with the true tracer distribution, with a small amount of noise. This is also without any pre-processing, which can also be performed in certain embodiments of the subject invention to limit the noise and error even further.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

[1] Huang, Sung-Cheng, et al. "Quantitation in positron emission computed tomography: 2. Effects of inaccurate attenuation correction." *Journal of computer assisted tomography* 3.6 (1979): 804.

[2] Park, Sang-June, et al. "Evaluation of the combined effects of target size, respiratory motion and background activity on 3D and 4D PET/CT images." *Physics in medicine and biology* 53.13 (2008): 3661.

[3] Gould, K. Lance, et al. "Frequent diagnostic errors in cardiac PET/CT due to misregistration of CT attenuation and emission PET images: a definitive analysis of causes, consequences, and corrections." *Journal of Nuclear Medicine* 48.7 (2007): 1112-1121.

[4] Xia, Ting, Adam M. Alessio, and Paul E. Kinahan. "Limits of ultra-low dose CT attenuation correction for PET/CT." *Nuclear Science Symposium Conference Record (NSS/MIC), 2009 IEEE*. IEEE, 2009.

[5] Xia, Ting, et al. "Ultra-low dose CT attenuation correction for PET/CT." *Physics in Medicine and Biology* 57.2 (2012): 309.

[6] Chi, Pai-Chun Melinda, et al. "Design of respiration averaged CT for attenuation correction of the PET data from PET/CT." *Medical physics* 34.6 (2007): 2039-2047.

[7] Pan, Tinsu, et al. "Attenuation correction of PET images with respiration-averaged CT images in PET/CT." *Journal of Nuclear Medicine* 46.9 (2005): 1481-1487.

[8] Dawood, Mohammad, et al. "Lung motion correction on respiratory gated 3-D PET/CT images." *Medical Imaging, IEEE Transactions on* 25.4 (2006): 476-485.

[9] Chi, Pai-Chun Melinda, et al. "Design of respiration averaged CT for attenuation correction of the PET data from PET/CT." *Medical physics* 34.6 (2007): 2039-2047.

[10] Zaidi, Habib, and Bruce Hasegawa. "Determination of the attenuation map in emission tomography." *Journal of Nuclear Medicine* 44.2 (2003): 291-315.

[11] Welch, A., et al. "Attenuation correction in PET using consistency information." *Nuclear Science, IEEE Transactions on* 45.6 (1998): 3134-3141.

[12] Bronnikov, Andrei V. "Reconstruction of attenuation map using discrete consistency conditions." *Medical Imaging, IEEE Transactions on* 19.5 (2000): 451-462.

[13] Censor, Yair, et al. "A new approach to the emission computerized tomography problem: simultaneous calculation of attenuation and activity coefficients." *Nuclear Science, IEEE Transactions on* 26.2 (1979): 2775-2779.

[14] Nuyts, Johan, et al. "Simultaneous maximum a posteriori reconstruction of attenuation and activity distributions from emission sinograms." *Medical Imaging IEEE Transactions on* 18.5 (1999): 393-403.

[15] Dicken, Volker. "A new approach towards simultaneous activity and attenuation reconstruction in emission tomography." *Inverse Problems* 15.4 (1999): 931.

[16] Conti, Maurizio. "State of the art and challenges of time-of-flight PET." *Physica Medica* 25.1 (2009): 1-11.

[17] Karp, Joel S., et al. "Benefit of time-of-flight in PET: experimental and clinical results." *Journal of Nuclear Medicine* 49.3 (2008): 462-470.

[18] Rezaei, Ahmadreza, et al. "Simultaneous reconstruction of activity and attenuation in time-of-flight PET." *Nuclear Science Symposium and Medical Imaging Conference (NSS/MIC), 2011 IEEE*. IEEE, 2011.

[19] M. Defrise, A. Rezaei, and J. Nuyts, "Time-of-flight PET data determine the attenuation sinogram up to a constant," *Physics in Medicine and Biology* 57(4) 885-899 (2012).

[20] F. Noo, R. Clackdoyle, and J. D. Pack, "A two-step Hilbert transform method for 2D image reconstruction," *Physics in Medicine and Biology* 49(17), 3903-3923 (2004).

[21] W. Cong, A. Momose, and G. Wang, "Fourier transform-based iterative method for differential phase-contrast computed tomography," *Optics Letters* 37(11), 1784-1786 (2012).

[22] T. Kohler, B. Brendel, and E. Roessl, "Iterative reconstruction for differential phase contrast imaging using spherically symmetric basis functions," *Med phys.* 38, 4542-4545 (2011).

[23] Rezaei, Ahmadreza, Johan Nuyts, and Michel Defrise. "Analytic reconstruction of the attenuation from 3D time-of-flight PET data." *Nuclear Science Symposium and Medical Imaging Conference (NSS/MIC), 2012 IEEE*. IEEE, 2012.

[24] Chartrand, Rick. "Numerical differentiation of noisy, nonsmooth data." *ISRN Applied Mathematics* 2011 (2011).

What is claimed is:

1. A system for performing a time-of-flight (TOF) positron emission tomography (PET) scan, the system comprising:
    a PET scanner configured to perform TOF PET scanning;
    at least one processor; and
    a machine-readable medium, in operable communication with the PET scanner and the at least one processor, having machine-executable instructions stored thereon that, when executed by the at least one processor, perform a method, the method comprising:
        obtaining an initial estimated attenuation singoram of a TOF PET scan, of the PET scanner, that has an unknown constant shift;
        determining the constant shift of the initial estimated attenuation singoram using the total amount of tracer provided to the subject of the TOF PET scan, wherein
    determining the constant shift is done without using any further information other than TOF PET scan data; and
        determining the attenuation sinogram for the TOF PET scan using the determined constant shift and the initial estimated attenuation sinogram.

2. The system according to claim 1, wherein the method executed by the at least one processor further comprises:
    reconstructing the TOF PET image using the attenuation sinogram and TOF PET data from the TOF PET scan.

3. The system according to claim 2, wherein the method executed by the at least one processor further comprises:
    performing pre-processing of the TOF PET data, before reconstructing the TOF PET image, to correct for random coincidences, estimate and subtract scattered photons, correct for detector dead-time, and/or correct for detector sensitivity.

4. The system according to claim 1, wherein determining the constant shift of the initial estimated attenuation singoram using the total amount of tracer provided to the subject comprises using the following equation:

$$e^{C(\theta)}\int_s m(\theta,s)\exp(g'(s,\theta))ds = \int_s\int_{-\infty}^{\infty} f(s\cdot\cos\theta - l\cdot\sin\theta, s\cdot\sin\theta + l\cdot\cos\theta)dlds = P,$$

where $m(\theta, s)$ is emission data along a path $(\theta, s)$, where $\theta$ is an angle of the path and $s$ is a distance along the path, where $g'(s, \theta)$ is the derivative of the Radon transform, where $f(x,y)$ is a distribution of the tracer, where $C(\theta)$ is the constant shift of the initial estimated attenuation singoram, and where $P$ is the total amount of tracer provided to the subject.

5. The system according to claim 2, wherein the system is configured for two-dimensional (2D) image reconstruction or three-dimensional (3D) image reconstruction, and
wherein the system is configured to perform a scan on a human patient or a non-human animal patient.

6. The system according to claim 1, further comprising a memory in operable communication with the processor and the machine-readable medium,
wherein the memory stores the TOF PET scan data, and
wherein the memory further stores data of the total amount of tracer provided to the subject of the TOF PET scan.

7. The system according to claim 2, further comprising a display in operable communication with the processor and the machine-readable medium,
wherein the display displays to a user of the system the determined attenuation sinogram for the TOF PET scan, and
wherein the display further displays to the user the reconstructed TOE PET image.

8. The system according to claim 1, wherein the PET scanner comprises a plurality of scanning rings, forming a generally cylindrical shape of scanning rings, wherein each scanning ring comprises a scintillating material on an inner surface thereof.

9. A system for determining an attenuation sinogram for a time-of-flight (TOF) positron emission tomography (PET) scan, the system comprising:
at least one processor; and
a machine-readable medium, in operable communication with the at least one processor, having machine-executable instructions stored thereon that, when executed by the at least one processor, perform a method, the method comprising:
obtaining an initial estimated attenuation singoram of a TOF PET scan that has an unknown constant shift;
determining the constant shift of the initial estimated attenuation singoram using the total amount of tracer provided to the subject of the TOF PET scan, wherein
determining the constant shift is done without using any further information other than TOF PET scan data; and
determining the attenuation sinogram for the TOF PET scan using the determined constant shift and the initial estimated attenuation sinogram.

10. The system according to claim 9, wherein determining the constant shift of the initial estimated attenuation singoram using the total amount of tracer provided to the subject comprises using the following equation:

$$e^{C(\theta)}\int_s m(\theta,s)\exp(g'(s,\theta))ds = \int_s\int_{-\infty}^{\infty} f(s\cdot\cos\theta - l\cdot\sin\theta, s\cdot\sin\theta + l\cdot\cos\theta)dlds = P,$$

where $m(\theta, s)$ is emission data along a path $(\theta, s)$, where $\theta$ is an angle of the path and $s$ is a distance along the path, where $g'(s, \theta)$ is the derivative of the Radon transform, where $f(x,y)$ is a distribution of the tracer, where $C(\theta)$ is the constant shift of the initial estimated attenuation singoram, and where $P$ is the total amount of tracer provided to the subject.

11. The system according to claim 9, wherein the system is configured to determine the attenuation sinogram for the TOF PET scan based on a 2D image reconstruction mode or based on a 3D image reconstruction mode.

12. The system according to claim 9, further comprising a memory in operable communication with the processor and the machine-readable medium,
wherein the memory stores the TOF PET scan data, and
wherein the memory further stores data of the total amount of tracer provided to the subject of the TOF PET scan.

13. The system according to claim 9, further comprising a display in operable communication with the processor and the machine-readable medium,
wherein the display displays to a user of the system the determined attenuation sinogram for the TOF PET scan, and
wherein the display further displays to the user a reconstructed TOF PET image.

14. A method for performing a time-of-flight (TOF) positron emission tomography (PET) scan on a subject, the method comprising:
providing a tracer to the subject to be scanned;
scanning the subject in a PET scanner configured to perform TOF PET scanning; and
determining an attenuation sinogram for the TOF PET scan,
wherein determining the attenuation sinogram for the TOF PET scan comprises:
obtaining an initial estimated attenuation singoram of the TOF PET scan, that has an unknown constant shift;
determining the constant shift of the initial estimated attenuation singoram using the total amount of tracer provided to the subject of the TOF PET scan, wherein
determining the constant shift is done without using any further information other than TOF PET scan data; and
determining the attenuation sinogram for the TOF PET scan using the determined constant shift and the initial estimated attenuation sinogram.

15. The method according to claim 14, further comprising:
reconstructing the TOF PET image using the attenuation sinogram and TOF PET data from the TOF PET scan.

16. The method according to claim 15, further comprising:
performing pre-processing of the TOF PET data, before reconstructing the TOF PET image, to correct for random coincidences, estimate and subtract scattered photons, correct for detector dead-time, and/or correct for detector sensitivity.

17. The method according to claim 14, wherein determining the constant shift of the initial estimated attenuation singoram using the total amount of tracer provided to the subject comprises using the following equation:

$$e^{C(\theta)}\int_s m(\theta,s)\exp(g'(s,\theta))ds = \int_s\int_{-\infty}^{\infty} f(s\cdot\cos\theta - l\cdot\sin\theta, s\cdot\sin\theta + l\cdot\cos\theta)dlds = P,$$

where $m(\theta, s)$ is emission data along a path $(\theta, s)$, where $\theta$ is an angle of the path and $s$ is a distance along the path, where $g'(s, \theta)$ is the derivative of the Radon transform, where f(x,y) is a distribution of the tracer, where $C(\theta)$ is the constant shift of the initial estimated attenuation singoram, and where P is the total amount of tracer provided to the subject.

18. The method according to any of claim 15, wherein the image is reconstructed using 2D image reconstruction or 3D image reconstruction, and wherein the subject is a human patient or a non-human animal patient.

19. The method according to claim 15, further comprising:

storing the TOF PET scan data on a memory;

storing data of the total amount of tracer provided to the subject of the TOF PET scan on the memory;

displaying the determined attenuation sinogram for the TOF PET scan on a display; and displaying the reconstructed TOF PET image on the display.

20. The method according to any of claim 14, wherein the PET scanner comprises a plurality of scanning rings, forming a generally cylindrical shape of scanning rings, wherein each scanning ring comprises a scintillating material on an inner surface thereof, and wherein: a) providing the tracer to the subject comprises injecting the subject with the tracer; b) the tracer is a radioactive tracer; or c) both.

* * * * *